United States Patent
Pawlikowski et al.

(10) Patent No.: US 7,574,368 B2
(45) Date of Patent: Aug. 11, 2009

(54) SYSTEM AND METHOD FOR UPGRADING A PRESSURE GENERATING SYSTEM

(75) Inventors: James Pawlikowski, Aspinwall, PA (US); Andrew L. Shissler, Delmont, PA (US); Michael T. Kane, Delmont, PA (US); Winslow K. Duff, Export, PA (US)

(73) Assignee: RIC Investments, LLC, Wilmington, DE (US)

( * ) Notice: Subject to any disclaimer, the term of this patent is extended or adjusted under 35 U.S.C. 154(b) by 731 days.

(21) Appl. No.: 10/016,506

(22) Filed: Dec. 10, 2001

(65) Prior Publication Data

US 2002/0077856 A1 Jun. 20, 2002

Related U.S. Application Data

(60) Provisional application No. 60/256,021, filed on Dec. 15, 2000.

(51) Int. Cl.
*G06Q 10/00* (2006.01)

(52) U.S. Cl. .............................. 705/2; 705/3; 600/300; 600/301

(58) Field of Classification Search .................. 705/2–4; 600/300–301
See application file for complete search history.

(56) References Cited

U.S. PATENT DOCUMENTS

| | | | |
|---|---|---|---|
| 5,456,692 A | | 10/1995 | Smith, Jr. et al. |
| 5,715,390 A | * | 2/1998 | Hoffman et al. ............... 726/20 |
| 5,725,559 A | * | 3/1998 | Alt et al. ......................... 607/5 |
| 5,800,473 A | | 9/1998 | Faisandier |
| 5,843,138 A | | 12/1998 | Evers et al. |
| 5,881,379 A | * | 3/1999 | Beier et al. ................. 707/101 |
| 5,901,311 A | * | 5/1999 | Labatte et al. ................. 713/2 |
| 6,094,702 A | * | 7/2000 | Williams et al. ............ 711/101 |
| 6,158,433 A | * | 12/2000 | Ong et al. .............. 128/204.21 |
| 6,305,374 B1 | * | 10/2001 | Zdrojkowski et al. .. 128/204.21 |

(Continued)

FOREIGN PATENT DOCUMENTS

JP 63-251879 10/1988

(Continued)

OTHER PUBLICATIONS 1993-024925, Feb. 1993, Derwent Patent.*

(Continued)

*Primary Examiner*—Gerald J. O'Connor
*Assistant Examiner*—Vivek D. Koppikar
(74) *Attorney, Agent, or Firm*—Michael W. Haas

(57) ABSTRACT

A method of upgrading a medical device having a controller that controls operation of the medical device according to an operating routine executed by the controller. Upgrading the medical device includes communicating an external device, such as a conventional computer, with the controller. An external access key is provided to the external device and compared to an internal access key provided by the medical device. Upgrading of the medical device is enabled if the two access keys match. Upgrading includes modifying or rewriting the operating routine stored in the medical device. A medical device manufacturer, supplier, or seller controls the distribution of the external access keys, thereby providing the ability to track the medical devices being upgraded and the upgrade provided to that device.

44 Claims, 4 Drawing Sheets

U.S. PATENT DOCUMENTS

| | | | |
|---|---|---|---|
| 6,385,593 | B2 | 5/2002 | Linberg |
| 6,504,825 | B1 * | 1/2003 | Atkins et al. ................ 370/254 |
| 2001/0034673 | A1 | 10/2001 | Yang et al. |
| 2001/0047314 | A1 | 11/2001 | Linberg |
| 2002/0026223 | A1 * | 2/2002 | Riff et al. .................... 607/27 |

FOREIGN PATENT DOCUMENTS

| | | |
|---|---|---|
| JP | 2000-140113 | 5/2000 |
| JP | 2000-510733 | 8/2000 |
| WO | WO 97/43004 | 11/1997 |
| WO | WO 00/29064 | 5/2000 |
| WO | WO 00/67827 | 11/2000 |
| WO | WO 01/56654 A1 | 8/2001 |
| WO | WO 01/60452 A1 | 8/2001 |
| WO | WO 02/49259 A2 | 6/2002 |

OTHER PUBLICATIONS

Abstract printed from Derwent database Cambell et al., "Manufacturing and Inventory Control for Medical Devices . . .", Pub. No. WO 200160452, published Aug. 23, 2001.

Brief Translation of Japanese Patent Disclosure No. 63-251879.

European Supplementary Search Report, Jan. 16, 2007.

\* cited by examiner

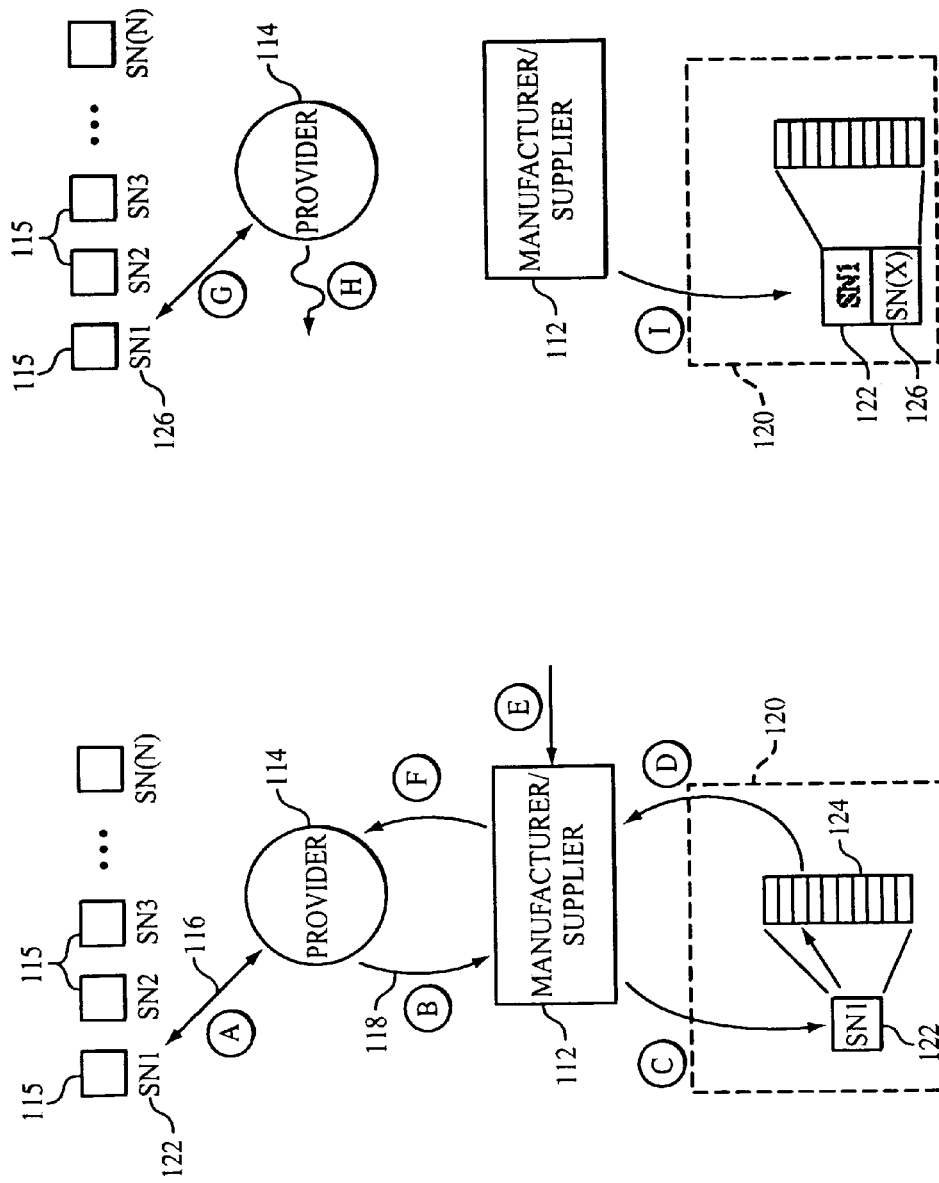

ized repair facility. The manufacturer or repair facility must disassemble the unit and physically replace the PROM with an upgraded PROM or other upgraded data storage device. Although this process is burdensome and requires that the patient forgo the use of the medical device while the device is being upgraded, it does allow the manufacturer, supplier, or seller of the medical device to keep track of which medical devices have been upgraded. For example, the manufacturer can create and maintain a database that contains a listing the medical devices and their upgraded status.
SYSTEM AND METHOD FOR UPGRADING A PRESSURE GENERATING SYSTEM

CROSS-REFERENCE TO RELATED APPLICATIONS

This application claims priority under 35 U.S.C. § 119(e) from provisional U.S. patent application No. 60/256,021 filed Dec. 15, 2000.

BACKGROUND OF THE INVENTION

1. Field of the Invention

The present invention pertains to a system and method of upgrading the operating features of a medical device, and, in particular, to a system and method in which an access key associated with both the medical device and the desired set of operating features for that medical device is used to gain access to and set the operating features of that medical device, thereby effectively controlling access to the ability to upgrade the operating features for security, regulatory, and product tracking purposes.

2. Description of the Related Art

A wide variety of electronically controlled medical devices that provide an equally wide variety of medical services, ranging from monitoring the condition of a patient to providing a medical treatment, are known and used everyday throughout the world. Such electronically controlled medical devices are used, for example, in hospitals, physician's offices, clinical sites, an ambulatory environment, as well as in patient's homes to meet the medical needs of the patient. A common feature of all electronically controlled medical devices is that a microprocessor executes an operating routine to control the functionality of the medical device.

Many such electronically controlled medical devices are specifically designed and manufactured so that the finished medical device operates according to a single set of operating features that does not change over the life of the medical device. That is, these devices are capable of executing only one operating routine every time the device is used, with no user selected or input variables. For example, a conventional pulse oximeter monitors a patient's arterial oxygen concentration, a conventional electroencephalograph monitors a patient's brain waves, and a conventional electrocardiograph monitors a patient's heartbeat. The monitoring function of each of these medical devices, which is established by the operating routine executed by the processor in these devices, does not change over the life of the product.

For purposes of the present invention, the phrase "operating feature" refers to any functional capability of the medical device. This includes features that are determined or set at the time of manufacture and cannot be altered by the user. This also includes features of the medical device that can be set, selected, or adjusted by an authorized technician or caregiver, examples of which are discussed in greater detail below.

It can be appreciated that the need may arise for the operating features of a medical device to be upgraded or altered. For example, an error in the operating routine may be discovered after manufacture and need corrected, or later versions or revisions of an operating routine may be developed as technology progresses. Good manufacturing and business practices, as well as government regulations, dictate that manufacturers, sellers or suppliers of medical devices have the ability to track the medical devices they sell. This is important, for example, if the need should arise for the medical devices to be recalled.

If a medical device uses a programmable read-only memory (PROM) to store the operating routine, upgrading the operating features of that device is very burdensome, requiring returning the medical device to the manufacturer or an authorized repair facility. The manufacturer or repair facility must disassemble the unit and physically replace the PROM with an upgraded PROM or other upgraded data storage device. Although this process is burdensome and requires that the patient forgo the use of the medical device while the device is being upgraded, it does allow the manufacturer, supplier, or seller of the medical device to keep track of which medical devices have been upgraded. For example, the manufacturer can create and maintain a database that contains a listing the medical devices and their upgraded status.

If the medical device uses an erasable programmable read-only memory (EPROM) to store the operating routine, also referred to as a flash memory, the device can be upgraded without disassembling the unit. Instead, reprogramming the EPROM can be done using any conventional reprogramming technique via a data port, which is typically provided on the external surface of the housing. While, this significantly simplifies the upgrade process, it can make it more difficult for the manufacturer, supplier, or seller of the medical device to track of which medical devices have been upgraded.

It is common in the medical industry for a manufacturer, supplier, or seller of medical devices to sell or lease a number of identical medical devices to a medical device provider or dealer, who then distributes the medical devices to the doctors' offices, hospitals, or to the patients directly. Upgrading of the medical devices in the medical device provider's or dealer's inventory, or in the field, can be done by the medical device provider/dealer, if the medical device uses an EPROM storage, and if the manufacturer, supplier, or seller provides the upgraded operating routine to the medical device provider/dealer. However, in this situation, the manufacturer of the medical devices has no way of knowing which medical devices in the medical device provider's inventory were actually upgraded by the medical provider. The manufacturer must rely on the medical device provider or dealer actually performing the upgrade to report accurately and reliably which device or devices have been upgraded. As a result, the manufacturer, supplier or seller does not have full control over which medical devices the provider/dealer actually upgrades, what upgrades is made to each device, and cannot track the upgrading of the various devices under the control of the provider/dealer without help from the provider/dealer.

Other electronically controlled medical devices exist in which at least some of the operating features of the medical device can be set after the device has been manufactured. For example, it is well know to use a pressure support system to provide a flow of gas to an airway of a patient at an elevated pressure via a patient circuit to treat a medical disorder. One such system, known as a continuous positive airway pressure (CPAP) device, supplies a flow of breathing gas at a constant positive pressure to the airway of a patient throughout the patient's breathing cycle to treat obstructive sleep apnea (OSA), cheynes-stokes respiration, congestive heart failure, central sleep apnea, as well as other cardio-respiratory disorders.

The ability of a pressure support system to provide a continuous pressure, as opposed, for example, to a variable pressure, is an operating feature of the system that is determined at the time of manufacture. The specific CPAP pressure that the device is to deliver, which is typically not set when the device leaves the manufacturer, is an example of an operating feature of the system that is determined after manufacture.

Instead, the CPAP pressure is set to a prescription level once a patient has been prescribed the CPAP device. Setting the CPAP pressure is accomplished, for example, by manually setting a switch, dial, knob or other input device associated with the medical device. If the CPAP operates according to an operating routine stored on an EPROM, setting the CPAP pressure can be accomplished by downloading the CPAP pressure as an operating feature directly into the controller or the memory of the medical device via a dedicated RS232 port.

A conventional ventilator, such as the ESPRIT® Ventilator manufactured by Respironics of Pittsburgh, Pa., is an example of a pressure support system in which the pressure of gas delivered to the patient varies between inspiration and expiration so as to replace or supplement the patient's own ventilation. For purposes of the present invention, the phase "pressure support system" or "pressure support device" includes any medical system or device, invasive or non-invasive, that delivers a flow of breathing gas to the airway of a patient, including a ventilator.

A conventional ventilator is capable of operating in a variety of ventilatory modes, where each mode corresponds to a different technique by which the ventilator controls its four basic ventilator operations. These four basic operations are: 1) determining of the trigger point, which is the transition from the expiratory to the inspiratory phase of the ventilatory cycle, 2) controlling the ventilator during the inspiratory phase where the ventilator delivers the flow of breathing gas, 3) determining the cycle point, which is the transition from the inspiratory phase to the expiratory phase, and 4) controlling the ventilator during the expiratory phase.

What the ventilator does in each mode of ventilation is typically determined at the time of manufacture, so that the ventilator always operates the same way each time a particular ventilatory mode is selected. However, which ventilatory mode the ventilator is to operate in, and the particular parameters of that mode, are generally not set when the ventilator leaves the factory. These operating features are set by the caregiver based on the needs of the patient when the patient begins using the ventilator. What the ventilator does in each ventilator mode, the selection of which mode to operate in, and the selectable parameters associated with each mode are considered the operating features of the ventilator for present purposes.

It is known to provide a pressure support device in which the pressure of the breathing gas delivered to the patient varies in synchronization with the patient's breathing cycle, so that a lower pressure is delivered to the patient during the expiratory phase of the breathing cycle than is delivered during the inspiratory phase. As a result, the patient receives the necessary pressure support during inspiration to treat their disorder, such as OSA, but is not breathing out against a relatively high pressure during expiration, which can be uncomfortable to some patients. This mode of pressure support is typically referred to as "bi-level" pressure support.

With bi-level pressure support, the patient's inspiratory positive airway pressure (IPAP), expiratory positive airway pressure (EPAP), and how the device detects and compensates for system leaks, if any, are examples of operating features of the pressure support system. Bi-level pressure support is taught, for example, in U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., the contents of each of which are incorporated by reference into the present invention.

It is further known to provide a pressure support therapy in which the pressure provided to the patient changes based on the detected conditions of the patient, such as whether the patient is snoring or experiencing an apnea, hypopnea, upper airway resistance, or a combination thereof. This mode of pressure support is typically referred to as an "auto-titration" mode, because the pressure support device itself determines the optimum pressure to deliver to the patient. With this type of pressure support system, the operating features typically include a maximum and/or minimum pressure that can be output by the device, which is set once the pressure support system has been prescribed to a patient, and the technique by which the system alters the patient pressure, which is typically set at the time of manufacture.

An example of an auto-titration pressure support system that adjusts the pressure delivered to the patient based on whether or not the patient is snoring is the Virtuoso® CPAP family of devices manufactured and distributed by Respironics, Inc. This auto-titration pressure support mode is taught in U.S. Pat. Nos. 5,203,343; 5,458,137 and 6,087,747 all to Axe et al., the contents of which are incorporated herein by reference. An example of a pressure support device that actively tests the patient's airway to determine whether obstruction, complete or partial, could occur and adjusts the pressure output to avoid this result is the Tranquility® Auto CPAP device, also manufactured and distributed by Respironics, Inc. This auto-titration pressure support mode is taught in U.S. Pat. No. 5,645,053 to Remmers et al., the content of which is incorporated herein by reference.

Other pressure support systems that offer other modes of providing positive pressure to the patient are also known. For example, a proportional assist ventilation (PAV®) mode of pressure support provides a positive pressure therapy in which the pressure of gas delivered to the patient varies with the patient's breathing effort to increase the comfort to the patient. U.S. Pat. Nos. 5,044,362 and 5,107,830 both to Younes, the contents of which are incorporated herein by reference, teach a pressure support device capable of operating in a PAV mode. Proportional positive airway pressure (PPAP) devices deliver breathing gas to the patient based on the flow generated by the patient. U.S. Pat. Nos. 5,535,738; 5,794,615; and 6,105,573 all to Estes et al., the contents of which are incorporated herein by reference, teach a pressure support device capable of operating in a PPAP mode. In the PAV and PPAP pressure support systems, the percent of assistance provided by the unit is at least one of the operating features of the pressure support device that is set after the device has been prescribed for use by a patient.

It should be noted that, as a medical device, the operating features of a pressure support system are normally determined for each patient under strict medical supervision to ensure that each patient receives the appropriate pressure support treatment for his or her condition. Prescribing a pressure support treatment for a patient is analogous to prescribing a medication necessary to cure the patient's ailment. However, instead of receiving medicine, the patient receives a durable medical product, such as a CPAP device, to treat his or her condition. As with a medication prescription, the patient's pressure support prescription should not be altered, except under a doctor's prescription, and must be followed, as prescribed, in order for the pressure support treatment to be effective. For these reasons, access to the ability to change the operating features of the medical device must be tightly controlled to prevent unauthorized tampering or inadvertent modification, which can be detrimental to the patient's health or reduce the efficacy of the treatment.

Other operating features include enabling or disabling additional features of the pressure support device, such as alarms, the ability to provide a time backup breath, which is a ventilatory breath that is delivered to the patient if he or she does not spontaneously initiate a breathing within a set period of time. A further operating feature common in many pressure support devices is a pressure ramp, which is a feature in which the pressure level provided to the patient is gradually increased over time. This is done, for example, to allow the patient to fall asleep under a relatively low pressure or to provide a comfortable transition from an initial low pressure to the desired therapeutic pressure. The duration of the ramp period is also an operating feature of a pressure support device. As with the operating features associated with the prescription pressure discussed above, activating, deactivating or altering other features of the pressure support system is preferably and, in many cases, necessarily done by an authorized caregiver or technician under the direction and/or supervision of the physician or other caregiver responsible for that patient.

As noted above, for purposes of the present invention, the operating features of the pressure support system include the type of pressure support treatment or mode provided to the patient by the pressure support system, e.g., CPAP, bi-level, auto-titration, PPAP, PAV, or a combination thereof. While a great number of pressure support systems can only operate in one pressure support mode, some conventional pressure support systems can operate in different pressure support modes depending on how the flexibility of the system. For example, a typical bi-level pressure support system can operate as a CPAP device if the IPAP and EPAP levels are the same. As noted above, a conventional ventilator is also typically capable of operating in one of several ventilatory modes.

Once a patient is prescribed a pressure support treatment, to minimize cost, he or she will receive or will purchase or lease a pressure support device that is only capable of operating in that pressure support mode. For example, it would not be economical or practical to issue a pressure support device capable of delivering bi-level pressure support to a patient who needs only a CPAP pressure support therapy, especially since the patient may need to be switched to a bi-level pressure support therapy.

On the other hand, it can be appreciated that for some patients, the need may arise for the medical device they are using to be switched to a different operating features over the course of their diagnosis and/or treatment. For example, it is also not uncommon to need to change the prescription pressure output by the pressure support device, the duration of the pressure ramp, or other the features of the system, over the course of the patient's support therapy. It is also not uncommon for an OSA sufferer to initially be treated with a CPAP device, and, thereafter, switched to a bi-level device in order to increase their comfort and compliance with the pressure support therapy. In addition, in certain situations, medical reimbursement policies dictate that a patient be treated with a first type of pressure support therapy before a reimbursement will be authorized for a second type of therapy.

However, as noted above, current techniques for upgrading a medical device do not provide the ability of the medical device manufacture, supplier, or seller to track and control the upgrade of medical devices done by someone beyond their control, such as a medical device provider or dealer who buys medical devices from the manufacturer. This is particularly the case for those features of a medical device that are intended to be altered after manufacture.

For example, a conventional bi-level pressure support system provides the ability to set the IPAP and EPAP pressure to be delivered to the patient. However, other than operating the bi-level device as a CPAP device, as discussed above, changing the bi-level device to any other mode of pressure support, such as a PPAP, auto-titration, or PAV, or to provide a timed backup breath or other feature not already included in the device, involves the same tracking and control problems discussed above with upgrading a PROM-based medical device.

SUMMARY OF THE INVENTION

Accordingly, it is an object of the present invention to provide a method of upgrading a medical device that overcomes the shortcomings of conventional upgrading techniques. This object is achieved according to one embodiment of the present invention by providing a method of upgrading a medical device that includes providing a medical device having a controller that controls the operation of the medical device according to an operating routine executed by the controller. A set of operating features for the medical device is determined based on the operating routine, and an internal access key is associated with each set of operating features of the medical device. The method further includes providing an external device that communicates with the controller, establishing a communication link between the external device and the controller, and inputting an external access key to the external device. The internal access key provided by the medical device is compared with the external access key. Upgrading of the medical device is made possible by enabling the operating routine to be modified if the internal access key matches the external access key. Changing the operating routine changes the operating features of the medical device.

It is yet another object of the present invention to provide a medical device upgrading system that does not suffer from the disadvantages associated with conventional upgrading system. This object is achieved by providing a medical device upgrading system comprising a medical device including (1) a controller that controls operation of the medical device according to an operating routine executed by the controller and (2) a memory, associated with the controller, that stores the operating routine. A set of operating features of the medical device is determined based on the operating routine, and an internal access key resident in or generated by the medical device is associated with each set of operating features of the medical device. An external device communicates with the controller via a communication link between the external device and the controller. The external device is also adapted to receive an external access key. The controller and external device communicate with one another so that controller or the external device can compare the internal access key with the external access key. If they match, upgrading of the medical device is permitted by enabling the operating routine to be modified.

It is a further object of the present invention to provide a method of processing and tracking an upgrade of a medical device that does not suffer from the shortcomings of conventional techniques for altering the operating features of a medical device. This object is achieved by providing a method of processing and tracking an upgrade of a medical device that includes first identifying a medical device to be upgraded, and providing an upgrade request from an upgrade requester to a medical device supplier. For purposes of the present invention, a supplier includes a manufacturer or seller or the other party desiring to track the upgrades of medical devices.

The upgrade request includes a first product identifier associated with the medical device to be upgraded and a requested upgrade of the medical device. The method further includes maintaining a database, which is available to the medical device supplier, that includes the first product identifier for the medical device and an external access key associated with both the medical device and an available upgrade. The database is accessed by the medical device supplier to determine an external access key associated with both the medical device to be upgraded and the requested upgrade, and the external access key is provided to the requester. The method further includes comparing the external access key with an internal access key associated with the medical device, and enabling an upgrade of the medical device if the internal access key matches the external access key. In addition, the database is updated to indicate that the medical device having the first product identifier has been upgraded with the desired upgrade.

It is a still further object of the present invention to provide a method for a medical device supplier to process and track an upgrade of a medical device that does not suffer from the shortcomings of conventional techniques for altering the operating features of a medical device. This object is achieved by providing a method that includes receiving, from an upgrade requester, an upgrade request including a first product identifier associated with the medical device and a desired upgrade, and maintaining a database, which is available to the medical device supplier. The database includes the first product identifier for the medical device and an external access key associated with both the medical device and an available upgrade. The method includes accessing the database by the medical device supplier upon receiving the upgrade request to determine an external access key associated with both the medical device to be upgraded and the desired upgrade based on the first product identifier. The medical device supplier provides to the upgrade requester the external access key associated with the medical device and the desired upgrade so that the upgrade requester can introduce the upgrade to the medical device if the external access key matches an internal access key associated with the medical device. In addition, the database is updated to indicate that the medical device has been upgraded with the desired upgrade.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 5A and 5B are schematic diagrams illustrating a process by which a medical device manufacturer, supplier, or sellers controls and tracks the upgrades of the medical devices is sells or is responsible for according to the principles of the present invention.

DETAILED DESCRIPTION OF THE PRESENTLY PREFERRED EMBODIMENTS OF THE INVENTION

Figure 1:
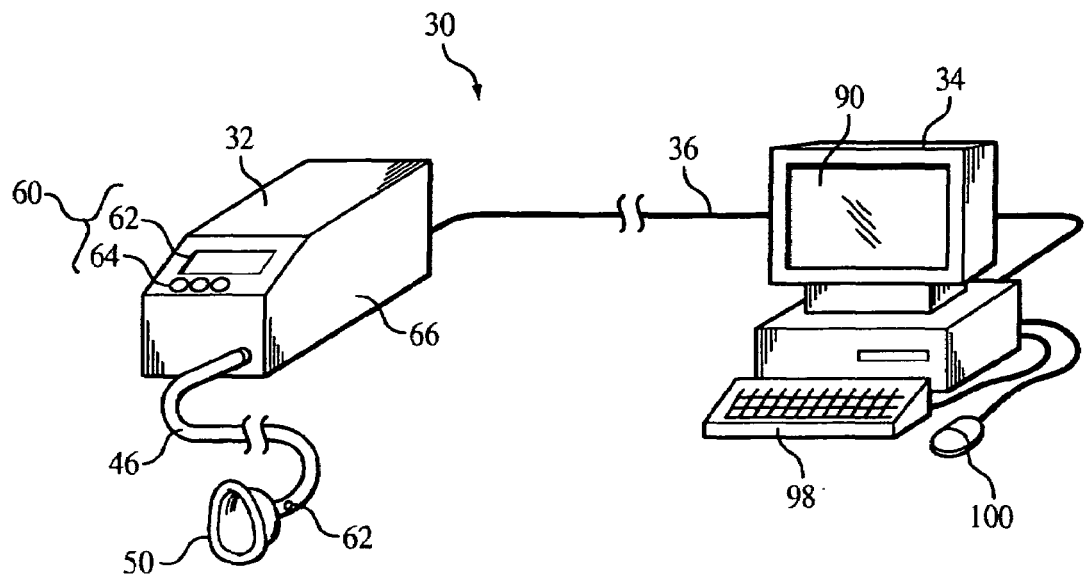
FIG. 1 is a perspective view of a system for upgrading the operating features of a medical device according to the principles of the present invention.

FIG. 1 schematically illustrates an exemplary embodiment of a medical system 30 that is adapted to be upgraded according to the principles of the present invention. In the illustrated embodiment, medical system 30 includes a medical device 32, which in this embodiment is a pressure support system, that generates a flow of breathing gas at an elevated pressure, and an external device 34 that communicates with pressure support system 32 via a communication link 36 for the purpose of upgrading the medical device.

As discussed in greater detail below, external device 34 is preferably a conventional computer, such as a laptop or personal computer, that can be readily transported to the site where the medical device is located, such as the patient's home, for accessing the medical device in the medical system. Of course, the present invention also contemplates the opposite, i.e., bringing medical device to the external device. The present invention enables the processing components of medical device 32 to communicate with the external device for purposes of upgrading the operation of the medical device, for example, by downloading an upgraded operating routine to the medical device, either in addition to or in place of the existing operating routine stored in the medical device.

A manufacturer, supplier or seller of the medical device has the ability to control and track the upgrade of each medical device under its control by limiting the ability to upgrade the medical device via the external device. According to the principles of the present invention, controlling and tracking the ability to upgrade the medical device is accomplished by providing an access key validation step in the medical device upgrade procedure, with the manufacturer, supplier or seller controlling the distribution of the access keys, and also, preferably, the distribution of the upgraded operating routine (software) that is provided to the medical device as a result of the upgrade.

Figure 2:
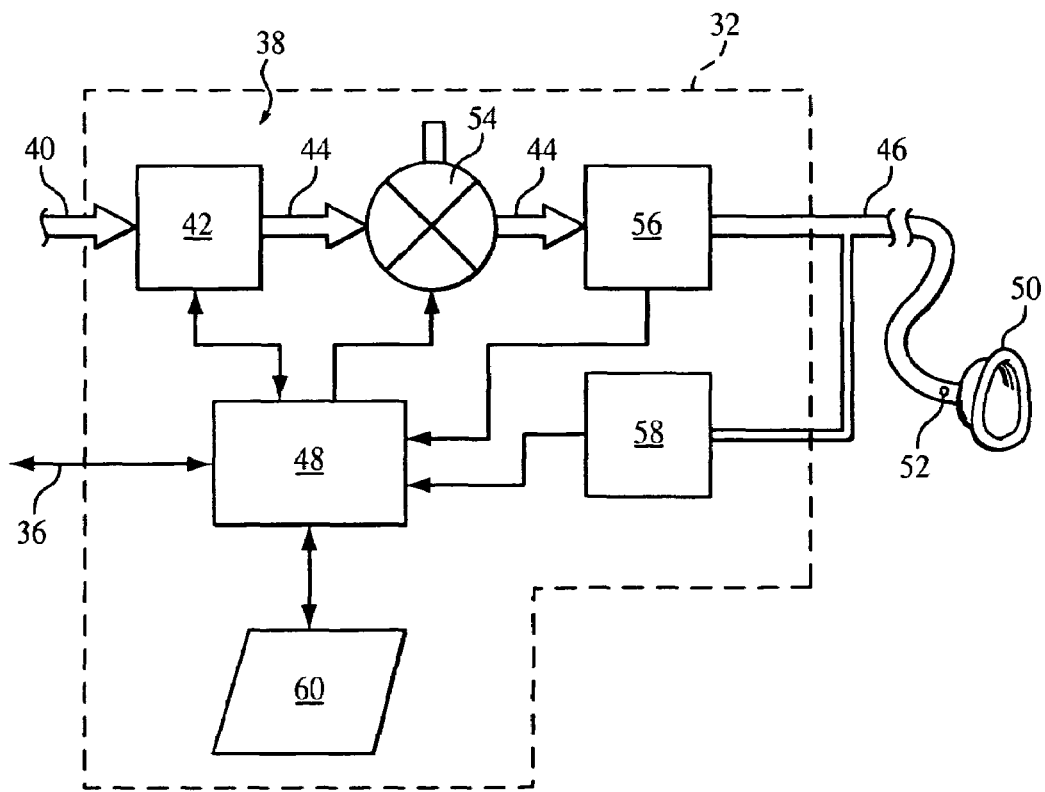
FIG. 2 is a schematic diagram of an upgradeable pressure support system according to the principles of the present invention.

As shown in FIG. 2, medical device 32 is a pressure support system that includes a pressure generating system, generally indicated at 38, that receives a supply of breathing gas from a breathing gas source, such as ambient atmosphere in the illustrated embodiment, and creates a flow of breathing gas at a pressure greater than the ambient atmospheric pressure. An inlet conduit 40 communicates breathing gas from the gas source to the inlet of a pressure generator 42. An exit conduit 44 communicates the flow of breathing gas from pressure generating system 38 to a patient circuit 46, which delivers the elevated pressure breathing gas to the airway of a patient. In an exemplary embodiment, pressure generator 42 is a centrifugal blower in which a fan or impeller is driven by a motor operating under the control of a controller 48.

It is to be understood, that the present invention contemplates other techniques for generating a flow of breathing gas at an elevated pressure. For example, a drag compressor, fan, piston, or bellows, can also be used as pressure generator 42 in pressure generating system 38 to create the flow of breathing gas at a pressure greater than the ambient atmospheric pressure.

In the illustrated embodiment, patient circuit 46 is a single-limb conduit having one end coupled to pressure support system 32 and a patient interface device 50 coupled to the other end. Patient interface device 50 connects the pressure generator 42 with the airway of the patient (not shown) so that the elevated pressure gas flow is delivered to the patient's airway. Examples of patient interface devices include a nasal mask, nasal and oral mask, full face mask, nasal cannula, oral mouthpiece, tracheal tube, endotracheal tube, hood, or any conventional device that is capable of communicating a flow of breathing gas with the airway of the patient.

Because patient circuit 46 in the illustrated embodiment is a single-limb circuit, an exhalation port 52, also referred to as an exhalation vent, exhaust port, or exhaust vent, is provided in the conduit to allow expired gas from the patient to exhaust to atmosphere. The present invention also contemplates that exhalation port 52 can be provided in the patient interface device in addition to or in the alternative to providing the port in the patient circuit.

The present invention further contemplates that the patient circuit can be a conventional two-limb patient circuit. In which case, the exhalation port at or near the patient interface device is eliminated. Instead, in a typical two-limb circuit, an exhaust conduit is coupled to the patient interface as the second limb. An exhaust valve, which operates under the control of controller 48, is provided in the exhaust conduit to control the flow of exhaust gas from the patient circuit. It is to be understood, however, that the present invention contemplates a variety of techniques for delivering the flow of breathing gas and/or controlling the exhaust of gas therefrom.

There are several techniques for controlling the pressure or flow of breathing gas delivered to the patient provided by pressure support system 32. One such method involves providing a pressure controller 54 in exit conduit 44. Pressure controller 54 exhausts a portion of the breathing gas in the exit conduit to atmosphere or to the inlet of pressure generator 42, restricts the flow of breathing gas through the exit conduit, or performs a combination of these two functions. Controller 48 preferably directs the operation of pressure controller 54 to regulate the pressure or flow of breathing gas provided to the patient. Examples of suitable pressure controllers are taught in U.S. Pat. No. 5,694,923 to Hete et al. and U.S. Pat. No. 5,598,838 to Servidio et al.

It is also known to control the speed of a motor driving pressure generator 42 so that pressure generator outputs the breathing gas at the desired flow or pressure. This motor speed control technique can be used alone to control the flow or pressure of the breathing gas provided to the patient, or it can be used in combination with a pressure controller 54, such as those discussed above. For present purposes, the combination of a pressure generator 38 and any of the above described techniques for controlling the flow or pressure of breathing gas provided to the patient, e.g., motor speed control, a pressure controller, or both, are referred to as a "pressure generating system," with the ultimate goal of the pressure generating system being to provide breathing gas to the airway of the patient at the desired pressure or flow.

The present invention contemplates that pressure support system 32 can include at least one sensor capable of measuring a characteristic associated with the flow of breathing gas, the pressure of the breathing gas, a condition of a patient using the pressure support system, a condition of the pressure support system, or any combination thereof. For example, FIG. 2 schematically illustrates a flow sensor 56 associated with exit conduit 44 and a pressure sensor 58 also associated with exit conduit 44 or patient circuit 46. The output from such sensors are provided to controller 48 and, depending on the operating mode of the pressure support system, used to control the rate of flow and/or pressure of the breathing gas delivered to the patient.

For example, in a bi-level pressure support system, cycling from IPAP to EPAP and triggering from EPAP to IPAP are based on the changes in the patient's breathing cycle, which is detected by such sensors. For an auto-titration pressure support system, the output of one or more such sensors is used to determine when to raise and lower the pressure provided to the patient, and can be used to determine the magnitude of the change in pressure. For example, U.S. Pat. No. 5,645,053 to Remmers et al., the content of which is again incorporated herein by reference, monitors patient flow to determine when and how to adjust the pressure applied to the patient.

It should be noted that the location and number of such sensors can be other than that shown in FIG. 2, so long as the function of providing feedback for the control of the pressure support system is achieved. In addition, it is also known to monitor the operation of the pressure generator to determine the condition of the patient, such as whether the patient in breathing on the system. In which case, the functions of the pressure and/or flow sensors are effectively incorporated into the pressure generator monitoring function.

Although sensors 56 and 58 are described above as being a flow and pressure sensor, respectively, it is to be understood that other types of sensors can be used in pressure support system 32. For example, a microphone can be provided to detect sounds produced by the patient, which can be used, for example, in an auto-titration pressure support system to control the pressure of the breathing gas delivered to the patient. See, e.g., U.S. Pat. Nos. 5,203,343 and 5,458,137 both to Axe et al., the contents of which are again incorporated herein by reference.

Other sensors that can be used with the pressure support system include a temperature sensor that senses the temperature of gas anywhere in the breathing circuit, a current and/or voltage sensor for sensing the current/voltage of the signal provided to the motor in the pressure generating system, and a tachometer that detects the rotational speed of the motor. These sensors are used, for example, to sense the condition of the patient, the flow or pressure of gas provided to the patient, or the operation of the pressure support system. Still other external sensors can include EMG electrodes provided on the patient, a respiratory belt that measures movement of the chest and/or abdomen, and a motion sensor to detect patient movement, such a leg movement.

In the illustrated exemplary embodiment, pressure support system 32 includes an input/output device 60 for communicating information to the user and for communicating information or commands to controller 48. An example of input/output device 60 is an LCD or LED display 62 and manually actuated buttons 64 provided on a housing 66 of pressure support system 32. Of course, the present invention contemplates other types of input/output devices, such as a keypad, voice activated input device, audio outputs, lights, switches, and knobs for use in providing between the user and the pressure support device. In addition, a data port coupled to controller 48 can also constitute input/output device 60 and can be used to establish communication link 36.

It is to be further understood that pressure support system 32 can include other components typically used by such systems. Examples of such ancillary components include a bacteria filter and a humidifier coupled to or provided in the patient circuit.

Figure 3:
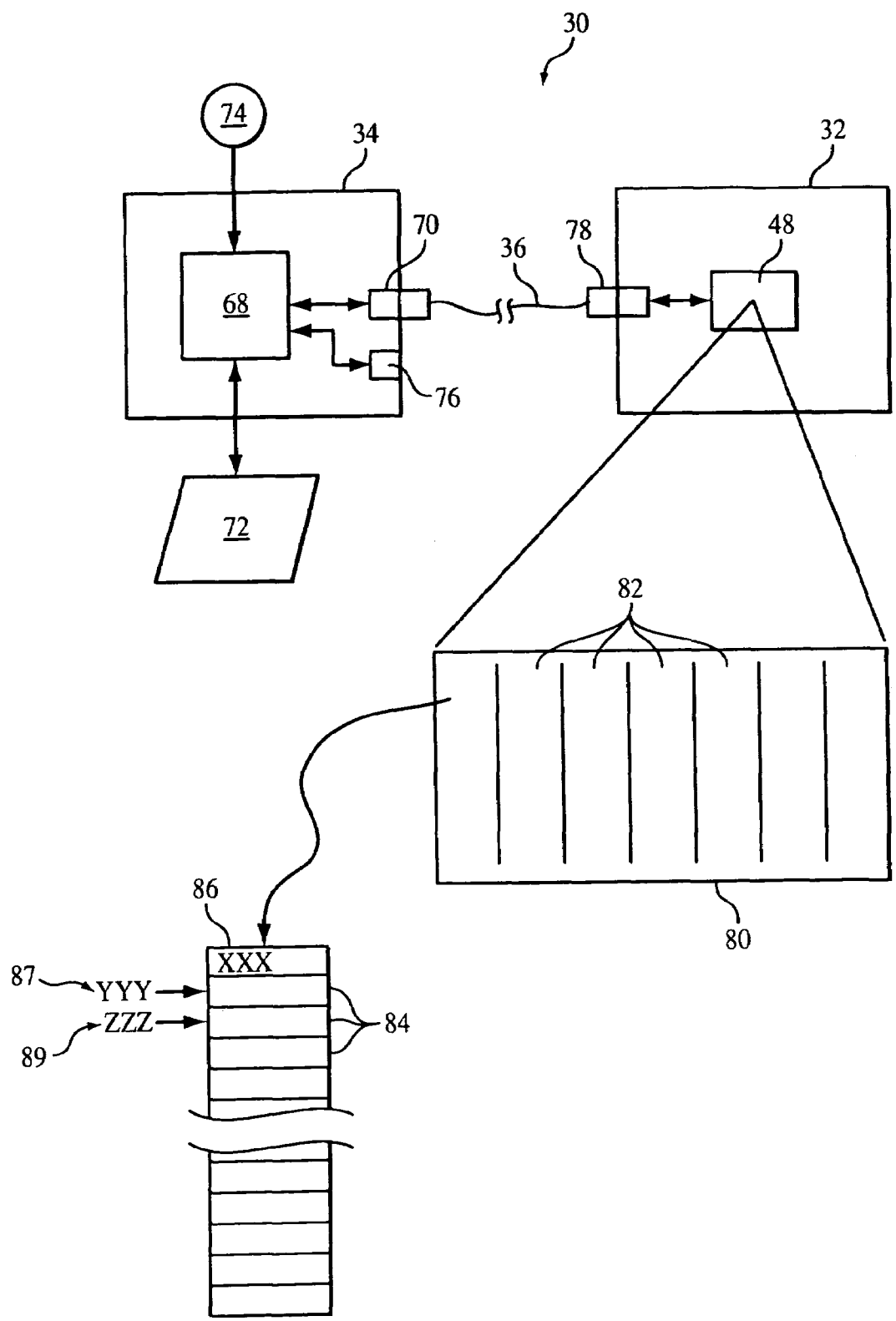
FIG. 3 is a schematic diagram illustrating one embodiment by which the operating features of a medical device are upgraded according to the principles of the present invention.

FIG. 3 illustrates one embodiment by which the operating features of a medical device are upgraded according to the principles of the present invention. In this embodiment, external device 34 includes a processing unit 68 that communicates with the medical device via a data port 70. External device also includes an input/output device 72 and the ability to read data from a distribution medium 74, such as a floppy disk reader, a compact disc read only memory (CD-ROM) reader, tape drive or any other conventional data reading device. Of course, external device 34 can include other features typically associated with a conventional computer, such as an audio input, audio output, ports for communicating with external devices, such as a printer, modem or link to other communication systems via any conventional communication protocol, additional data ports 76, and a hard drive (not shown).

Communication link 36 between processor 68 and controller 48 is accomplished by coupling a communication cable between a data port 70 in the external device and a data port 78 provided on the medical device for this purpose. In an exemplary embodiment of the present invention data ports 70 and 78 are RS 232 ports. It is to be understood, however, that the present invention contemplates any conventional technique for exchanging data between the external device and the medical device including a hardwired or wireless communication link.

As schematically shown in FIG. 3, controller 48 in medical device 32 includes a memory 80, such as a flash memory or EPROM. In the illustrated exemplary embodiment of the present invention, memory 80 is segregated in to a plurality of memory sections 82, each of which is individually erasable so that the entire memory or portions thereof can be eased and rewritten. Memory 80 stores the operating routine that is executed by the controller 48 each time the medical device is operated. The operating features of the medical device are determined based on this operating routine. For example, in order for medical device 32 to function as a non-invasive bi-level pressure support device (assuming that the medical device includes the necessary hardware such as that shown in FIG. 2) the operating routine must include the appropriate software for running the pressure generating system, controlling the pressure output by that system, detecting leaks (intentional and unintentional), compensating for such leaks, and triggering and cycling the pressure generating system.

In one of the sections of memory 80, or in a portion of a section, a plurality of access key memory locations 84 are allocated for storing a plurality of access keys, which are discussed in greater detail below. One embodiment of the present invention contemplates providing fifteen such access key memory locations, of course this number can be increased or decreased so long as there is at least one access key memory location.

In the illustrated embodiment, a first access key "xxx" is shown stored in a first access key memory location 86. The access keys of the present invention are preferably a sequence of alpha-numeric characters capable of being entered and processed by a conventional computer processing system. It is to be understood, however, that other characters can be used in the access key character sequence, including a single character. While FIG. 3 illustrates the remaining fourteen access key memory locations as being empty, it is to be understood that a default access key or other null data can be provided in these locations, so long as that data effectively indicates that the no valid or useable access key is stored therein.

As noted above, the operating features of the medical device are determined based on the operating routine that is stored in memory 80. In addition, an access key is associated with each set of operating features of the medical device. In effect, an access key is associated with each operating routine that is stored in memory 80 and capable of being carried out by the medical device. For example, in the illustrated embodiment, suppose that the internal access key "xxx" in the first memory location corresponds to the operating features of a CPAP device. Thus, in this example, the operating routine for causing the medical device to function as a CPAP device is stored in memory 80 and the access key "xxx" stored in the first memory location identifies the pressure support system as providing a CPAP mode of pressure support.

Depending on the functional flexibility of the medical device and the allocation of the parameters controlled by the access keys, a number of different access keys can be associated with a single medical device, with each access key identifying or corresponding to a unique set of operating features of that device. Preferably, the access key includes a portion that identifies the operating features associated with that access key and a key portion. At the time of manufacture, each of these access keys is determined, the operating features for that medical device associated with each access key is also known, as well as the product identifier for the medical device. All of this information is preferably stored in a database available only to the manufacturer, supplier or seller for tracking purposes described in detail below.

As the medical device is upgraded, a new access key associated with that upgrade, i.e., with the new set of operating features, is provided in the next available access key memory location. Suppose, for example, that the CPAP device is to be upgraded by changing the prescription pressure from its original value of 6 cm $H_2O$ to a new value of 8 cm $H_2O$. In which case, the operating routine can be modified, or completely rewritten, to cause the pressure support system to output 8 cm $H_2O$ and a new internal access key, such as "yyy" is written into the next available access key memory location, as indicated by arrow 87. Suppose, for example, that the CPAP device is again upgraded by changing the CPAP device to a bi-level device. The operating routine is modified or completely rewritten to cause the pressure support system function as a bi-level device (assuming of course that the pressure support system has the hardware supporting such a modification). Again, a new access key associated with the bi-level operating features, such as "zzz" is written into the next available access key memory location, as indicated by arrow 89.

Each time the medical device is operated, controller 48 checks to determine whether a valid access key is stored in the access key memory locations. In this embodiment, if more than one access key is stored in this memory array, the controller will look for the access key that was the latest to be input to the medical device, for example, based on its position in the access key memory array. Checking to determine whether a valid access key is stored in memory involves generating an internal access key or retrieving an internal access key from a secure memory location and comparing the internal access key to the access key stored in the access key memory array. If these keys match, the medical device is thus capable of operating according to the operating routine stored in memory 80. If the keys to not match, or if there is no access key stored in the access key memory array, the medical device will not function, or will function at a reduced capability.

The present invention also contemplates that the access keys stored in the access key memory array effectively unlocks or enable additional or different operating features of the medical device, so that the particular location of the access key in the access key memory array is not important. In this embodiment, the present invention contemplates that the operating routine stored in memory 80 is capable of providing a number of different operating features. The particular operating features that are enabled is determined based on what an access key or keys are stored in the access key memory array, which each access key unlocking a particular feature or set of features.

In this embodiment, when the medical device is upgraded, a new access key associated with that upgrade, i.e., with the additional set of operating features, is provided in any available access key memory location. Suppose, for example, that the medical device is a bi-level pressure support device capable of outputting a maximum pressure of 20 cmH$_2$O, and is to be upgraded by adding a timed back-up breath. In which case, a new access key associated with this additional operating feature is added to the access key memory array, and the operating routine can be modified or rewritten to cause the pressure support system to provided the timed back-up breath when appropriate.

It should be noted that the present invention also contemplates that the operating routine already existing in the medical device can include the appropriate programming to provide the timed back-up breath, but that the programming that provides is operating feature only becomes enabled when the new access key is added to the access key memory array. Thus, the addition of access keys to the access key memory array effectively adds additional features to the medical device, either by unlocking existing operating features or by enabling additional programming to be stored in memory 80 that provides these additional features.

Again, each time the medical device is operated, controller 48 checks to determine whether a valid access key is stored in the access key memory locations. In this embodiment, the controller processes all of the access keys available for that medical device to find all of the valid access keys stored in this memory array. As with the previous embodiment, checking to determine whether a valid access key is stored in memory involves generating the internal access keys or retrieving the internal access keys from a secure memory location and comparing the internal access keys to the access key or keys stored in the access key memory array. If more than one valid access key is determined, the medical device is able to provide the operating features associated with each access key. If the keys to not match, or if there is no access key stored in the access key memory array, the medical device will not function, or will function at a reduced capability.

Suppose that, in this example, the medical device is to again be upgraded to allow the pressure support system to provide 30 cmH$_2$O (assuming of course that the medical device hardware is capable of delivering this operating feature). This requires adding an additional valid access key to the access key memory array that effective allows the medical device to provide this increase pressure level. If necessary, additional programming can be downloaded from the external device to the controller at that time to allow the medical device to provide this additional operating feature.

It should be understood, that adding additional operating features is not necessarily intended to exclude the possibility that other operating features can be manually controlled or adjusted as done conventionally. For example, the present invention contemplates that the IPAP and EPAP levels in the bi-level pressure support device in the above example can still be manually set by the caregiver. The present invention merely allows the bi-level pressure support device to now allow the caregiver to select a pressure greater than 20 cmH$_2$O by not greater than 30 cmH$_2$O.

The present invention contemplates that the operating features that are actuated or enabled by the access keys stored in the access key memory array are additive to one another. Meaning that each operating feature added to the medical device builds upon an existing operating feature already enabled for that device. For example, one access key may allow the pressure support device to operate in a bi-level mode of pressure support, a second access key may allow the device to provide a timed backup breath, a third access key may enable the device to monitor patient compliance, a fourth access key may actuate certain alarms, and so on.

In addition, the present invention contemplates that the operating features that are actuated or enabled by the access keys stored in the access key memory array are cumulative but not necessarily additive. Meaning that each operating feature added to the medical device may provide its own unique set of features that can be selected by the user. For example, the access key memory array may be provided with two access keys, one key allows the pressure support device to function as a bi-level pressure support device, and the other key allows the pressures support device to function as a PAV pressure support device. If both keys are valid, the medical device enables the user to selected which of these two modes of ventilation are to be provided. Of course, if for some reason one of these keys is not valid, the medical device would not provide the mode of ventilation associated with the invalid key.

As noted above, in one embodiment of the present invention, the controller generates the appropriate internal access key for each memory location or for each operating feature that the medical device is capable of providing to check the validity of the access key currently residing at that location or anywhere in the access key memory array. Generating the appropriate internal access key for each memory location or for each operating feature is accomplished by running an access key determination algorithm. Preferably, this algorithm is permanently stored in the medical device is a non-erasable memory. The details of this algorithm should not be disclosed to the users of the medical device, because it could enable them to produce an access key without the authorization of the manufacture, supplier, or seller thereby defeating the purpose of present invention.

In another embodiment of the present invention, the internal access keys associated with the possible upgrades of the medical device are not generated using an algorithm, but are read from an non-erasable memory. Of course, appropriate security measures should be taken to ensure that these stored access key can not be downloaded or otherwise retrieved from the medical device without the authorization of the manufacture, seller or supplier who is interested in maintaining control over the upgrading of the medical devices.

Figure 4:
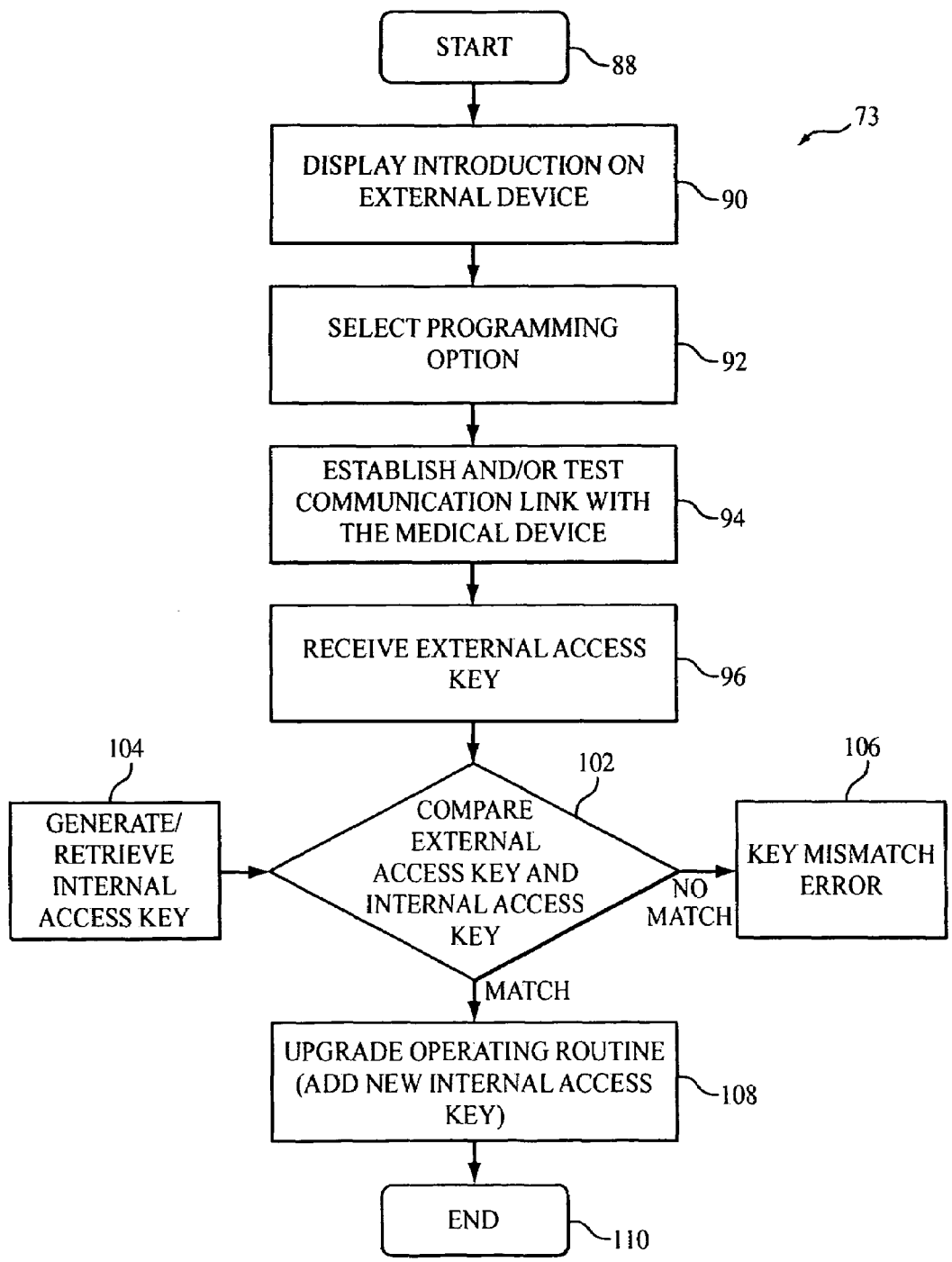
FIG. 4 is a flowchart illustrating an exemplary process for upgrading the operating features of a medical device according to the principles of the present invention.

With the external device and medical device configured to communicate with one another as shown, for example, in FIG. 3, a medical device upgrading process 73, an exemplary embodiment of which is shown in FIG. 4, is provided to the external device. In a preferred embodiment of the present invention, the algorithm for performing the medical device upgrading process is stored on distribution medium 74, which is any information storage medium magnetic, optical or otherwise, such as tape, floppy disc, memory chip, CD-ROM, and DVD, that is capable of being physically delivered to the provider or other entity performing the upgrade. The provider executes the medical device upgrading process, for example, by running the upgrade program stored in a CD-ROM on their computer 34. The present invention also contemplates, however, providing the algorithm for performing the medical device upgrading process using other conventional data transfer methods, such as downloading the upgrade software to the external device via a LAN, WAN, or internet communication link.

The medical device upgrading process is preferably presented to the provider, via external device 34, in the form of a wizard, which is step-by-step tutorial that prompts the user through each step of the upgrading process. The wizard process also allows the user to step forward or backward through the process and includes a cancel or abort capability that allows the user to end the upgrading process at any step.

As shown in FIG. 4, the medical device upgrading process begins with a start step 88 and proceeds to an introduction step 90. In step 90, the user of external device 34 is presented with an introductory display. This display preferably appears on a display terminal 90 of external device 34 (FIG. 1) or on any other output device associated with the external device. The contents of the introductory display can include any desired material, such as a welcome message, a message identifying the updating program and the medical devices it can be used to upgrade, advertising, legal messages (such as copyright, trademark, and patent notices), a summary of the upgrading procedure, help buttons (which, when actuated by the user, display various help messages), and the next instruction to be followed in order to upgrade the medical device. It should be noted that the present invention contemplates that the introductory display can include multiple pages with various page branches depending on the options selected by the user. For example, if the user selects a help option, one of several, further selectable help pages can be displayed. In addition, any computer animation or other presentation techniques can be used to present information to the user.

In reprogramming option selection step 92, the user is presented with the various reprogramming options that can be performed by the upgrading program. The present invention contemplates that various different upgrading programs can be provided on the same distribution medium, for example to minimize the number of different distribution mediums that must be kept in stock by the manufacturer, supplier, or seller. That is, instead of having three different distribution mediums each containing one upgraded operating routine, a single distribution medium can be provided having all three upgraded operating routines stored thereon. In step 92, the user selects which of the different upgraded operating routines is to be provided to the medical device.

The present invention contemplates that upgrading the operating features of the medical device includes any modification of the operating features of the device, as well as reprogramming the medical device without changing its operating features. For example, providing a new release or new version of the software currently being executed by the medical device. The term "upgrading" also includes reprogramming of the medical device that causes the device to have fewer operating features. For example, reprogramming an auto-titration device to function as a CPAP device, or eliminating certain features, such as an auto-on, auto-off capability, or compliance monitoring capability are also considered an upgrade. In short, "upgrading" a medical device includes downloading an operating routine to the device, no matter if the new operating routine replaces an existing routine or is the first routine stored in the device.

For example, the present invention contemplates that a medical device manufacturer may supply a medical provider with one or more medical device but not install the operating software on the medical device hardware. In which case, the medical device, at this stage, is essentially a compilation of hardware incapable of functioning as a medication device until programmed or only capable of functioning at a reduced capacity. The operating routine could then be furnished to the provider at a later date for installation on the medical devices. This manufacturing and distribution technique may prevent inadvertent, unauthorized or unintentional use of the medical device until the medical device manufacturer or seller furnishes the medical device operating routine.

In an exemplary embodiment of the present invention, the medical device is a noninvasive single-limb bi-level pressure support device. Such a device includes software that controls how the device detects leaks (intentional leaks in the mask or patient circuit as well as unintentional leaks at the mask-patient interface), compensates for such leaks, triggers and cycles, as well as accomplishes numerous other functions, such as compliance monitoring and alarm triggering. Possible upgrades for such as device include adding a timed backup breath, adjusting the IPAP level, EPAP level, or both, reinstalling the operating routine without making any functionality changes in the pressure support device, e.g., to correct a programming error in the existing operating routine or to provide the most recent release of the operating routine, or adding other modes of pressure support, such as a PAV, PPAP, or auto-titration mode, either in addition to or in place of the bi-level pressure support mode. In this exemplary embodiment, the user presented with two upgrade operations in step 92: (1) whether to upgrade the bi-level device by adding the timed backup breath, and (2) whether to upgrade the bi-level software only, without adding or deleting any operating features. The operating routine for each type of upgrade is preferably stored in a single information storage medium 74.

It should be further noted that the present invention contemplates that upgraded operating routines of entirely different medical devices or different models of similar devices can all be provided on a common distribution medium. As a result, the user of the distribution medium may be prompted to select that type of medical device being upgraded and the specific upgrade for that medical device in step 92.

Upon selecting the appropriate upgrade for the desired medical device, the upgrading process advances to communication link establishing step 94. In step 94, the external device and the controller in the medical device attempt to establish a communication link or to test whether a valid communication link with a medical device has been established. In an exemplary embodiment of the present invention, this is accomplished by causing processing unit 68 in the external device to select the appropriate communication protocol for the medical device and to provide a device available query to an available data port on the external device. The external device waits for a reply to the query from the medical device indicating that a valid communication link between the medical device and the external device has been established.

The present invention contemplates repeating this process for each available data port until a valid communication link is established. By providing a query on all ports and receiving a reply from one of these ports, the upgrading process automatically determines which data port is being used in the communication link, thereby avoiding the need for the user to manually select the appropriate data port for the communication link. Of course, this can also be done manually. If, after a certain number of tries, no data port is identified as providing a valid communication link with the medical device, a communication error message and/or instructions for connecting the external device to the medical device can be displayed.

The present invention contemplates that once a valid communication link is established, the external device and medical device will establish whether the medical device is a proper medical device for the upgrade selected, i.e., whether the medical device is capable of being upgraded in the manner selected. For example, the user attempts to upgrade a bi-level device by adding a timed backup breath, but connects the external device to a CPAP device, it will not be capable of implementing the selected upgrade. In which case, a device mismatch error message and/or instructions describing the correct medical device to be connected can be displayed.

Similarly, if the medical device has already been upgraded with the selected upgrade, an error message or other instructions can be provided to notify the user of this fact. The present invention also contemplates preventing an earlier version of an operating software from replacing a later version. Thus, if the user selects an upgrade option that would cause this result, an error message or other instructions can be provided to notify the user of this fact. Of course, other messages and instructions can be displayed depending on the error that prevented a proper communication link for the desired upgrade from being established.

If a valid communication link is established, medical device upgrading process 73 proceeds to an external access key entry step 96. In this step, the user is prompted to enter an external access key into the external device. This can be accomplished, for example, by manually entering the external access key via a keyboard 98 or mouse 100, or by downloading the external access key from a storage medium or other source. The present invention contemplates that the access key relates to both the medical device to be upgraded and to the selected operating feature or features to be upgraded. Thus, in order to install a certain set of operating features onto medical device by reprogramming that device with an operating routine that provides these features, an external access key for that medical device and matching that set of operating features, which was determined at the time of manufacture, must be input to the external device in step 96.

Once the external access key has been entered, the medical device upgrading process advances to an access key validation step 102, where the external access key is compared to an internal access key generated by the medical device in internal access key generation/retrieval step 104. The present invention contemplates the external device provides the external access key to controller 48 in medical device 32. When this occurs, the controller also executes step 104, and executes the internal access key generating algorithm to generate the internal access key associated with the selected upgrade option. As noted above, the present invention also contemplates storing all of the access key available to a medical device in a non-erasable, secure memory. In which case, step 104 involve retrieving the appropriate access key from the memory.

The present invention also contemplates that controller 48 compares the external access key with the internal access key. It is should be noted that this comparison step could take place in the external device. However, this would require that controller 48 download its internal access key generated in step 104 to the external device. In the interest of keeping the internal access keys secure, it is preferable that the internal access keys not be provided to the external device.

If the internal and external access keys do not match, controller 48 notifies the external device and an error message and/or other instructions provided to the user in access key mismatch step 106. If the internal and external access keys match, the upgrading process takes place in upgrade step 108 and memory 80 is rewritten or modified with a new operating routine provided by external device 34 from distribution medium 74. During this process, the external device preferably displays a status bar indicating the status of the upgrading process, for example, the amount of data or time left in the data transfer operation involved in rewriting memory 80.

In step 108, the next available access key memory location is loaded with the access key, either internal or external, from step 102. In an alternative embodiment, the access key, either internal or external, from step 102 is provided to any available access key memory array location. It does not matter which access key, internal or external, is loaded, since they are identical. The access key is loaded in the access key memory array for the reasons discussed above. Namely, each time the medical device is operated, the controller checks the internal access key, i.e., the key generated by the medical device in step 104, with the keys in the access key memory array. There must be a match before that device will operate with the set of operating feature associated with that access key. This is done to ensure that the medical device is not upgraded without authorization, i.e., without the proper access key.

When the data transfer is complete and the external access key has been rewritten into the last available access key memory location, the process ends in termination step 110. Preferably, an "upgrade complete" display is provided to notify the user that the medical device has been successfully upgraded with the new operating routine.

The process by which a medical device manufacturer or sellers controls and tracks the upgrades of its medical devices according to the principles of the present invention is described below with reference to FIGS. 5A and 5B. These figures schematic illustrate two parties typically involved in the medical device manufacture and distribution process, a medical device manufacturer 112 and a medical device provider 114. It should be understood, however, that the techniques of the present invention are not limited to these two parties. On the contrary, the manufacturer in FIGS. 5A and 5B can be a medical device supplier or seller rather than an original equipment manufacturer (OEM), who receives a supply of medical devices from an OEM. Likewise, provider can include any entity in the supply chain that is responsible for a medical device, including a health maintenance organization (HMO), hospital, physician, or even an individual patient.

The medical upgrade process begins in step A, as indicated by arrow 116, with provider 114 identifying which medical device 115 is to be upgraded and the desired upgrade for that medical device. This includes determining the manufacturer's product identifier 122, such as a model and serial number (SN), for the particular medical device to be upgraded. This information is provided by the provider to the manufacturer in step B, as indicated by arrow 118, in any conventional manner.

Manufacturer 112 maintains a database 120 of all the medical devices under its control. This database includes the product identifier 122, i.e., serial number, for each device, and a list of access keys 124 associated with the medical device having that serial number. Of course, database 120 can also include other information about the medical device, such as the current upgrade configuration for that device, date sold, any repair or recall information or history, and any other information. As noted above, each access key corresponds to an available upgrade for the medical device.

Upon receiving the product identifier and desired upgrade, the manufacturer accesses database 120 in step C to determine whether the requested upgrade is available for medical device identified. If the medical device can support the requested upgrade, an external access key associated with the medical device and the desired upgrade is retrieved from the database in step D. In addition, the desired upgrade, i.e., the desired upgraded operating routine to be downloaded to the medical device is also received by the manufacturer in step E.

As noted above, in an exemplary embodiment of the present invention, the upgraded operating routine is preferably stored on a storage medium for easy delivery to the provider. The external access key and the storage medium containing the upgraded operating routine are delivered to the provider via any conventional delivery technique. For example, the present invention contemplates providing the upgraded operating routine on a CD-ROM and providing the external access key on a label adhered to the packaging accompanying the CD-ROM. Of course, these two items can be provided separately, and can be provided to the provider in a variety of ways.

For example, both the upgraded operating routine and the external access key can be provided to the provider via the internet. The present invention also contemplates that the upgraded operating routine can be provided on a disc and the external access key provided via an audio voicemail system that the provider accesses upon receiving the upgraded operating routine. Other combinations by which these two items can be delivered from the manufacturer to the provider are too numerous to discuss in detail. The present invention also contemplates that the upgraded operating routine can be provided directly from the CD-ROM maker to the provider, without having to go to the manufacturer.

Once the provider has both the upgraded operating routine and the external access key, they can upgrade the selected medical device in step G according to the upgrade procedure set forth above with respect to FIG. 4. When the upgrade is completed, the provider discards the distribution medium containing the upgraded operating routine as well as the access key in step H. In addition, the manufacturer updates database 120 in step I to indicate that the medical device having that serial number has been upgraded.

While upgrading the database to indicate that a medical device has been upgraded can be accomplished in a variety of ways, the present invention contemplates assigning a new product identifier (serial number) 126 to that medical device in database 120. In effect, the upgraded medical device is operating as an entirely new medical device in the eyes of the manufacture, and, thus, is assigned a new product identifier. Preferably, the provider also places a new serial number on the medical device for use in future upgrades. However, the present invention also contemplates providing a cross-reference between the old serial number and the new serial number so that the medical device can be identified using either an old serial number or the new serial number. This technique for tracking a medical device upgrade is advantageous in that the same set of access key are associated with the medical device using its new serial number or an old serial number.

It can be appreciated from the above description of the present invention that the ability to upgrade a medical device is limited by the use of the access key. Furthermore, the access key limits the type of upgrade that can be provided to a given medical device. In both cases, an entity, such as the manufacturer, supplier or seller of the medical device is able, through the controlled distribution of the access keys, to control which medical device is upgraded and what upgrade is made to that device.

In the above embodiments, upgrading the medical device is accomplished by either modifying, in whole or in part, the operating routine stored in the medical device. It is to be understood that the present invention contemplates other techniques for altering the operating features, i.e., upgrading, the medical device. For example, several operating routines or sub-routines can be stored in the memory of the medical device. These routines or subroutines can be unlocked or locked by the upgrading process, thereby adding or removing operating features that were preprogrammed into the medical device.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method of upgrading a pressure generating system comprising:
providing a pressure generating system including (a) a pressure generator adapted to generate a flow of breathing gas, (b) a controller that controls operation of the pressure generator, (c) a memory storing a first operating routine wherein the controller controls operation of the pressure generator according to the first operating routine and a user defined setting, wherein a first set of operating features of the pressure generating system is determined based on the first operating routine, and wherein an internal access key is associated with each set of operating features of the pressure generating system;
providing an external device adapted to communicate with the controller;
establishing a communication link between the external device and the controller;
inputting an external access key to the external device;
comparing the internal access key provided by the pressure generating system with the external access key;
enabling upgrading of the pressure generating system by enabling the first operating routine to be replaced responsive to the internal access key matching the external access key;
upgrading the pressure generating system by replacing the first operating routine with a second operating routine and causing the controller to execute the second operating routine so that the pressure generating system operates according to a second set of operating features and the user defined setting;
maintaining a database for a plurality of pressure generating systems external to a pressure support systems, wherein the database includes (a) a serial number unique to each pressure generating system in the plurality of pressure systems, (b) one or more operating routines available to each pressure generating system in the plurality of pressure generating systems, and (c) external access keys associated with each of the one or more operating routines; and
updating the database by assigning a new serial number for an upgraded pressure generating system.

2. The method of claim 1, wherein upgrading the pressure generating system includes providing the second operating routine from the external device to the controller.

3. The method of claim 1, wherein the first set of operating features includes a first pressure support mode, and wherein the second set of operating features includes a second pressure support mode.

4. The method of claim 3, wherein (a) the first pressure support mode is a bi-level pressure support mode, and the second pressure support mode is a bi-level pressure support mode with a timed backup breath delivery capability, or (b) the first pressure support mode is a continuous positive airway pressure (CPAP) support mode and the second support mode is a variable positive airway pressure support mode in which the pressure delivered to the patient varies between inspiration and expiration.

5. The method of claim 1, wherein establishing the communication link includes providing a hard wired connection between the external device and the controller.

6. The method of claim 1, wherein inputting the external access key to the external device includes manually entering the external access key into the external device via a keypad associated with the external device, or reading the external access key from a memory associated with the external device.

7. The method of claim 1, further comprising downloading the external access key to the controller responsive to the internal access key being input to the external device, and wherein comparing the internal access key with the external access key takes place in the controller.

8. The method of claim 1, wherein each internal access key associated with each set of operating features of the pressure generating system is (1) generated by the controller based on an access key generating algorithm each time the comparing step is to be performed, or (2) stored in advance in a memory in the pressure generating system and recalled from the memory each time the comparing step is to be performed.

9. The method of claim 1, wherein each internal access key associated with each set of operating features of the pressure generating system is generated by the controller based on an access key generating algorithm each time the comparing step is to be performed, and further comprising storing the external access key in the pressure generating system as a new internal access key, and causing the controller to generate the new internal access key in a subsequent access key validation process.

10. A pressure generating system upgrading system, comprising
    a pressure generating systems including (a) a pressure generator adapted to generate a flow of breathing gas, (b) a controller that controls operation of the pressure generator, and (c) a memory associated with the controller that stores a first operating routine, wherein the controller control operation of the pressure generator according to the first operating routine and a user defined setting, wherein a first set of operating features of the pressure generating system is determined based on the first operating routine, and wherein an internal access key is associated with each set of operating features of the pressure generating system;
    an external device adapted to communicate with the controller via a communication link between the external device and the controller, wherein the external device is adapted to receive an external access key, and wherein the controller or the external device compares the internal access key of the pressure generating system with the external access key and upgrades the pressure generating system by replacing the first operating routine with a second operating routine responsive to the internal access key matching the external access key; and
    a database for a plurality of pressure generating systems, wherein the database includes (a) a serial number unique to each pressure generating system in the plurality of pressure systems, (b) one or more operating routines available to each pressure generating system in the plurality of pressure generating systems, and (c) external access keys associated with each of the one or more operating routines, and wherein the database is updated to assign a new serial number for an upgraded pressure generating system.

11. The system of claim 10, wherein the controller is adapted to receive the second operating routine from the external device responsive to the external access key matching the internal access key, and wherein the controller thereafter executes the second operating routine causing the pressure support system to operate according to the second set of operating features.

12. The system of claim 11, wherein (a) the first set of operating features corresponds to a bi-level pressure support mode, and the second set of operating features corresponds to a bi-level pressure support mode with a timed backup breath delivery capability or (b) the first pressure support mode is a continuous positive airway pressure (CPAP) support mode and the second support mode is a variable positive airway pressure support mode in which the pressure delivered to the patient varies between inspiration and expiration.

13. The system of claim 10, wherein the communication link is a hard wired connection between the external device and the controller.

14. The system of claim 10, wherein the external device includes a keypad by which the external access key is manually entered into the external device.

15. The system of claim 10, wherein the external device is adapted to download the external access key to the controller, and wherein comparing the internal access key with the external access key takes place in the controller.

16. The system of claim 10, wherein the controller is adapted to generate each internal access key associated with each set of operating features of the medical based on an access key generating algorithm executed by the controller each time an access key validation is required.

17. A pressure generating system upgrading system comprising:
    (a) a pressure generating system including:
        (1) a pressure generator adapted to generate a flow of breathing gas,
        (2) processing means for controlling at least one operation of the pressure generator according to a first operating routine executed by the processing means and a user defined setting, and
        (3) memory means, associated with the processing means, for storing the first operating routine, wherein a first set of operating features of the pressure generating system is determined based on the first operating routine, and wherein an internal access key is associated with each set of operating features of the pressure generating system;
    (b) an external device adapted to communicate with the processing means via a communication link between the external device and the processing means, wherein the external device includes means for receiving an external access key, wherein the processing means or the external device includes means for comparing the internal access key of the pressure generating system with the external access key and for upgrading the pressure generating system by replacing the first operating routine with a second operating routine responsive to the internal access key matching the external access key; and
    (c) a database for a plurality of pressure generating systems, wherein the database includes (1) a serial number unique to each pressure generating system in the plurality of pressure systems, (2) one or more operating routines available to each pressure generating system in the plurality of pressure generating systems, and (3) external access keys associated with each of the one or more operating routine, and wherein the database is updated to assign a new serial number for an upgraded pressure generating system.

18. The system of claim 17, wherein the processing means is adapted to receive the second operating routine from the external device responsive to the external access key matching the internal access key, and wherein the processing means thereafter executes the second operating routine causing the pressure support system to operate according to a second set of operating features.

19. The system of claim 18, wherein (a) the first set of operating features corresponds to a bi-level pressure support mode, and the second set of operating features corresponds to a bi-level pressure support mode with a timed backup breath delivery capability or (b) the first pressure support mode is a continuous positive airway pressure (CPAP) support mode and the second support mode is a variable positive airway pressure support mode in which the pressure delivered to the patient varies between inspiration and expiration.

20. The system of claim 17, wherein the communication link is a hard wired connection between the external device and the processing means.

21. The system of claim 17, wherein the external device includes a keypad by which the external access key is manually entered into the external device.

22. The system of claim 17, wherein the external device is adapted to download the external access key to the processing means, and wherein comparing the internal access key with the external access key takes place in the processing means.

23. The system of claim 17, wherein the processing means is adapted to generate each internal access key associated with each set of operating features of the medical based on an access key generating algorithm executed by the processing means each time an access key validation is required.

24. The system of claim 17, wherein the processing means generates each internal access key associated with each set of operating features of the pressure generating system based on an access key generating algorithm each time an access key validation process is to be performed, stores the external access key in the memory as a new internal access key, and generates the new internal access key in a subsequent access key validation process.

25. A method of processing and tracking an upgrade of a pressure generating system, comprising:
    identifying a pressure generating system to be upgraded;
    providing an upgrade request from an upgrade requester to a pressure generating system supplier, wherein the upgrade request includes a first serial number associated with the pressure generating system to be upgraded and a requested upgrade of the pressure generating system;
    maintaining a database for a plurality of pressure generating systems, available to the pressure generating system supplier, wherein the database includes (a) the first serial number for each pressure generating system in the plurality of pressure generating systems, (b) one or more upgrades available to each pressure generating system in the plurality of pressure generating systems, and (c) an external access keys associated with both the pressure generating system and an available upgrade from the one or more for that pressure generating system;
    accessing the database, by the pressure generating system supplier, to determine an external access key associated with both the pressure generating system to be upgraded and the requested upgrade;
    providing the external access key to the pressure generating system;
    comparing the external access key with an internal access key associated with the pressure generating system;
    upgrading the pressure generating system responsive to the internal access key matching the external access key; and
    wherein upgrading the pressure generating system comprises replacing a first operating routine with a second operating routing and causing a controller to execute the second operating routine so that the pressure generating system operates according to a second set of operating features and a user defined setting; and
    updating the database to indicate that the pressure generating system having the first serial number has been upgraded with the desired upgrade by assigning a new serial number for an upgraded pressure generating system.

26. The method of claim 25, wherein providing the external access key to the pressure generating system includes providing the desired upgrade to the upgrade requester via a distribution media or a electronic communication link.

27. The method of claim 26, wherein providing the external access key and the desired upgrade includes providing the external access key on a first medium and providing the desired upgrade on a second medium.

28. The method of claim 25, wherein comparing the external access key with an internal access key takes place in the pressure generating system to be upgraded.

29. The method of claim 25, wherein updating the database includes providing a second serial number associated with the pressure generating system.

30. The method of claim 25, wherein the pressure generating system includes a controller that controls operation of the pressure generating system according to an operating routine executed by the controller, wherein a set of operating features of the pressure generating system is determined based on the operating routine, wherein the internal access key is associated with each set of operating features of the pressure generating system; and
    wherein providing the external access key to the pressure generating system comprises:
        providing an external device adapted to communicate with the controller,
        establishing a communication link between the external device and the pressure generating system, and
        inputting an external access key to the external device.

31. The method of claim 30, further comprising, after the enabling step, upgrading the pressure generating system by providing an upgraded operating routine from the external device to the controller, wherein the controller thereafter executes the upgraded operating routine causing the pressure generating system to operate according to an upgraded set of operating features.

32. The method of claim 31, further comprising providing the upgraded set of operating features to the external device from the pressure generating system supplier.

33. The method of claim 31, wherein each internal access key associated with each set of operating features of the pressure generating system is generated by the controller based on an access key generating algorithm each time the comparing step is to be performed, and further comprising storing the external access key in the pressure generating system as a new internal access key, and causing the controller to generate the new internal access key in a subsequent access key validation process.

34. The method of claim 30, wherein the pressure generating system is a pressure support system comprising a pressure generating system adapted to generate a flow of breathing gas, wherein the controller executes a first operating routine to control the operation of the pressure generating system according to a first set of operating features.

35. The method of claim 34, further comprising, after the enabling step, upgrading the pressure generating system by providing a second operating routine from the external device to the controller, wherein the controller thereafter executes the second operating routine causing the pressure support system to operate according to a second set of operating features.

36. The method of claim 35, wherein the first set of operating features includes a first pressure support mode, and wherein the second set of operating features includes a second pressure support mode.

37. The method of claim 36, wherein (a) the first pressure support mode is a bi-level pressure support mode, and the second pressure support mode is a bi-level pressure support mode with a timed backup breath delivery capability or (b) the first pressure support mode is a continuous positive airway pressure (CPAP) support mode and the second support mode is a variable positive airway pressure support mode in which the pressure delivered to the patient varies between inspiration and expiration.

38. The method of claim 30, wherein establishing a communication link includes providing a hard wired connection between the external device and the controller.

39. The method of claim 30, wherein inputting an external access key to the external device includes manually entering the external access key into the external device via a keypad associated with the external device, or reading the external access key from a memory associated with the external device.

40. The method of claim 30, wherein comparing the internal access key with the external access key takes place in the controller.

41. The method of claim 30, wherein each internal access key associated with each set of operating features of the pressure generating system is (1) generated by the controller based on an access key generating algorithm each time the comparing step is to be performed, or (2) stored in advance in the pressure generating system and recalled from memory each time the comparing step is to be performed.

42. A method for a pressure generating system supplier to process and track an upgrade of a pressure generating system:
receiving, from an upgrade requester, an upgrade request including first serial number associated with the pressure generating system and a desired upgrade;
maintaining a database for a plurality of pressure generating systems, available to the pressure generating system supplier, wherein the database includes (a) the first serial number for each pressure generating system in the plurality of pressure generating systems, (b) one or more upgrades available to each pressure generating system in the plurality of pressure generating systems and (c) an external access keys associated with both the pressure generating system and an available upgrade from the one or more upgrades for that pressure generating system;
accessing the database, by the pressure generating system supplier, responsive to receiving the upgrade request, to determine an external access key associated with both the pressure generating system to be upgraded and the desired upgrade based on the first serial number;
providing, from the pressure generating system supplier to the upgrade requester, the external access key associated with the pressure generating system and the desired upgrade so that the upgrade requester can introduce the upgrade to the pressure generating system responsive to the external access key matching an internal access key associated with the pressure generating system; and
upgrading the pressure generating system by replacing a first operating routine with a second operating routing and causing a controller to execute the second operating routine so that the pressure generating system operates according to a second set of operating features and the user defined setting; and
updating the database to indicate that the pressure generating system has been upgraded with the desired upgrade by assigning a new serial number for an upgraded pressure generating system.

43. The method of claim 42, wherein providing the external access key and the desired upgrade includes providing the external access key in a first medium and the desired upgrade in a second medium.

44. The method of claim 42, wherein updating the database includes providing a second serial number associated with the pressure generating system.

* * * * *